United States Patent [19]
Stolz-Dunn et al.

[11] Patent Number: 5,723,624
[45] Date of Patent: Mar. 3, 1998

[54] PROCESS FOR THE PREPARATION OF 5-ARYL-2,4-DIALKYL-3H-1,2,4-TRIAZOLE-3-THIONES

[75] Inventors: Sandra K. Stolz-Dunn, Midland; David H. Louks, Saginaw, both of Mich.; Yolanda M. Puga, Morgan Hill, Calif.; Christian T. Goralski, Midland, Mich.

[73] Assignee: Merrell Pharmaceuticals Inc., Cincinnati, Ohio

[21] Appl. No.: 765,013

[22] PCT Filed: Jun. 1, 1995

[86] PCT No.: PCT/US95/06927

§ 371 Date: Mar. 28, 1997

§ 102(e) Date: Mar. 28, 1997

[87] PCT Pub. No.: WO96/01812

PCT Pub. Date: Jan. 25, 1996

Related U.S. Application Data

[63] Continuation of Ser. No. 271,925, Jul. 7, 1994, abandoned.

[51] Int. Cl.$^6$ .................................................. C07D 249/12
[52] U.S. Cl. ............................................................ 548/263.2
[58] Field of Search .................................................. 548/263.2

[56] References Cited

U.S. PATENT DOCUMENTS 4,775,688  10/1988  Kane et al. .
4,912,095  3/1990   Kane et al. .
5,236,942  8/1993   Miller .

FOREIGN PATENT DOCUMENTS 0221485  5/1987  European Pat. Off. .
2287172  5/1976  France .

OTHER PUBLICATIONS

Kane, John M. et al, *J. Med Chem.*, vol. 31, (1988), pp. 1253–1258.

Chemical Abstracts, vol. 109, No. 23, No. 211093q, p. 671 (1988).

*Primary Examiner*—Patricia L. Morris
*Attorney, Agent, or Firm*—Nelsen L. Lentz

[57] ABSTRACT

The present invention relates to a a novel process for preparing 5-aryl-2,4-dialkyl-3H-1,2,4-triazole-3-thiones which have been shown to have antidepressant activity and are useful in the treatment of Wernicke-Korsakoff syndrome and Alzheimer's disease.

12 Claims, No Drawings

PROCESS FOR THE PREPARATION OF 5-ARYL-2,4-DIALKYL-3H-1,2,4-TRIAZOLE-3-THIONES

This application is a continuation of application Ser. No. 08/271,925, filed Jul. 7, 1994, now abandoned, and had an effective international filing date of Jun. 1, 1995 as application PCT/US95/06927 which designated the U.S. and entered the U.S. National Phase on Dec. 19, 1996 under 35 USC 371.

BACKGROUND OF THE INVENTION

The present invention relates to a novel process for preparing 5-aryl-2,4-dialkyl-3H-1,2,4-triazole-3-thiones which have previously been shown to have antidepressant activity as disclosed in U.S. Pat. No. 4,775,688, issued Oct. 4, 1988 and in U.S. Pat. No. 4,912,095, issued Mar. 27, 1990. In addition they have been shown to be useful in the treatment of Wernicke-Korsakoff syndrome as disclosed in U.S. Pat. No. 5,100,906, issued Mar. 31, 1992, and in the treatment of Alzheimer's disease as disclosed in U.S. Patent No. 5,236,942, issued Aug. 17, 1993.

The present invention provides the 5-aryl-2,4-dialkyl-3H-1,2,4-triazole-3-thiones in a single step. The present invention also eliminatese isolation of the intermediate coupled compound and further avoids formation of significant quantities of the generally highly insoluble intermediate compound, while maintaining formation of the desired product in high yield. The 5-aryl-2,4-dialkyl-3H-1,2,4-triazole-3-thiones are isolated directly from the reaction medium by crystallization from a suitable solvent to afford high quality products.

SUMMARY OF THE INVENTION

The present invention provides a novel process for preparing a compound of the formula:

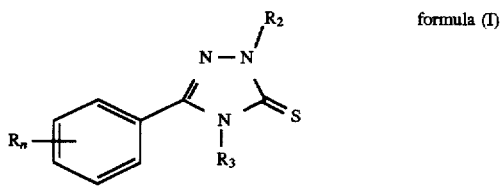

formula (I)

wherein

R is halogen, $C_{1-3}$ alkyl or $C_{1-3}$ alkoxy;

n is the integer 1 or 2; and $R_2$ and $R_3$ are each independently $C_{1-3}$ alkyl, comprising;

a) mixing a compound of the formula:

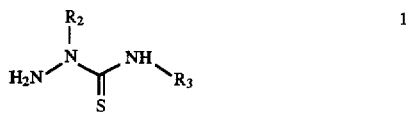

1 wherein $R_2$ and $R_3$ are defined as above, with a base and an organic solvent;

b) agitating the mixture at a temperature of about 22° C. to reflux; and c) adding about one molar equivalent of a compound of the formula:

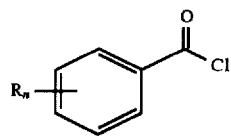

2 wherein R and n are defined as above, to the mixture.

DETAILED DESCRIPTION OF THE INVENTION

As used herein the term "$C_{1-3}$ alkyl" refers to a saturated straight or branched chain hydrocarbon radical of one to three carbons. Included within the scope of this term are methyl, ethyl, n-propyl and isopropyl. The term "$C_{1-3}$ alkoxy" refers to an alkyloxy radical made up of an oxygen radical bearing a saturated or branched chain hydrocarbyl radical of one to three carbon atoms and specifically includes methoxy, ethoxy, propyloxy and isopropyloxy. As used herein the term "halogen" or "halo" refers to a fluorine, chlorine or bromine atom. When n is the integer 1, R may be located at the ortho (position 2), meta (position 3) or para (position 4) position on the phenyl ring. When n is the integer 2, R may be in any of the 2,3-; 2,4-; 2,5-; 2,6-; 3,4-; and 3,5- positions on the phenyl ring.

The process of the present invention is set forth in Scheme I. All the substituents, unless otherwise indicated, are previously defined. The reagents and starting materials are readily available to one of ordinary skill in the art. For example, the general preparation of compounds of structures (1) and (2) are described in U.S. Pat. No. 4,775,688, issued Oct. 4, 1988 and in U.S. Pat. No. 4,912,095, issued Mar. 27, 1990.

Scheme I

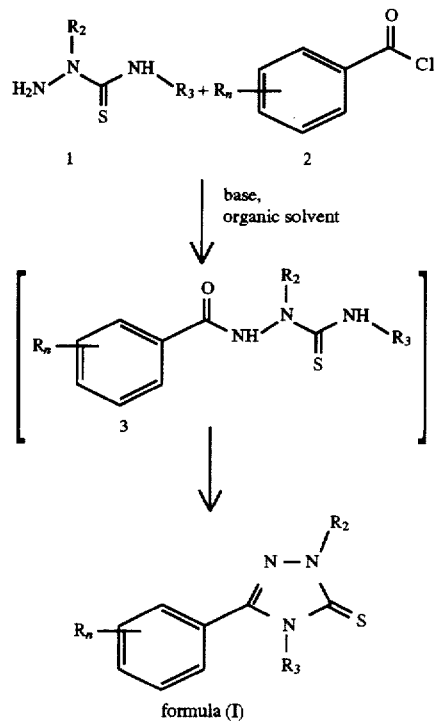

formula (I)

In Scheme I, the dialkylthiosemicarbazide (1) is mixed with a suitable base and a suitable organic solvent under an inert atmosphere, such as nitrogen. Examples of a suitable organic solvent are any halocarbon solvent, such as methylene chloride, chloroform, carbon tetrachloride and the like, benzene or a substituted aromatic solvent which contains one or more lower alkyl, alkoxy or halo substituents, such as toluene, o-xylene, m-xylene, p-xylene, chlorobenzene, bromobenzene, anisole and the like. Toluene is the preferred organic solvent. In addition, the reaction can be carried out in the absence of organic solvent. Examples of suitable bases are aqueous bases, such as aqueous sodium hydroxide, aqueous potassium hydroxide, aqueous lithium hydroxide, aqueous sodium bicarbonate, aqueous sodium carbonate and the like, or trialkylamine and pyridine bases, such as triethylamine, tripropylamine, tributylamine, diisopropylethylamine, pyridine and the like. The preferred bases are aqueous sodium hydroxide and triethylamine. The most preferred base is aqueous sodium hydroxide. The aqueous sodium hydroxide may be in a concentration of from 4% to 50% by weight in water. The number of equivalents of base added to the solution can vary from 1.001 to 3.0 equivalents. The preferred number of equivalents added to the solution is 1.01 to 2.2 equivalents.

The above mixture is then agitated at a temperature ranging from 22° C. to the reflux temperature of the organic solvent employed. The preferred temperature of the mixture is about 60° to 100° C. and the most preferred temperature is about 80° C. Approximately one equivalent of the acid chloride (2) is then added slowly to the mixture. The acid chloride (2) may be added to the mixture either neat or as a solution in a suitable organic solvent, such as toluene. It is preferred that neat acid chloride be added to the heated mixture. After addition of the acid chloride, the reaction mixture is allowed to stir until the reaction is complete. The reaction mixture is then processed by techniques well known in the art, such as extractive methods and crystallization. For example, if heated, the reaction mixture may be cooled to room temperature and the resulting organic and aqueous layers separated wherein aqueous base was employed in the reaction. If a trialkylamine or pyridine base was utilized instead of aqueous base, approximately an equivalent volume of water is added to the reaction mixture with agitation followed by separation of the organic layer from the aqueous layer. The organic layer from either the aqueous base reaction or trialkylamine or pyridine reaction is then washed with water and concentrated under vacuum. The product is isolated by crystallization upon addition of a suitable solvent, such as isopropanol to provide the compounds of formula (I).

The following examples present typical syntheses as described by Scheme I. These examples are understood to be illustrative only and are not intended to limit the scope of the invention in any way. The reagents and starting materials are readily available to one of ordinary skill in the art. As used in the following examples, the following terms have the meanings indicated: "eq." refers to equivalents, "g" refers to grams, "mg" refers to milligrams, "mol" refers to moles, "mmol" refers to millimoles, "L" refers to liters, "mL" refers to milliliters, "°C." refers to degrees Celsius, "mm Hg" refers to millimeters of mercury, "GC" refers to gas chromatography, and "R$_t$" refers to retention time.

EXAMPLE 1

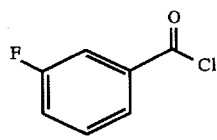

Preparation of 3-Fluorobenzoyl Chloride

A 100-mL, three-necked, round-bottomed flask, equipped with a reflux condenser, thermometer, nitrogen bubbler and magnetic stirring bar is charged sequentially with thionyl chloride (52.7 mmol, 6.28 g), toluene (40 mL), 3-fluorobenzoic acid (7.02 g, 50.1 mmol) and a catalytic amount of dimethylaminopyridine (DMAP). The funnel used for addition of the above reagents is rinsed with toluene (10 mL) which is also added to the reaction mixture. The reaction mixture is slowly heated to 60°–70° C. with stirring. The progress of the reaction is followed by gas chromatography wherein several drops of the reaction mixture are added to methanol to produce the methyl ester of the acid chloride. The methanol solution is allowed to stand for about 5 minutes at room temperature prior to GC analysis (GC analysis utilizes a Hewlett Packard 5890 Series II gas chromatograph on a 30 m×0.25 mm DB-5 capillary column; 60° C. for 5 minutes to 275° C. at a rate of 20° C./minute.; R$_t$ for methyl ester of 3-fluorobenzoic acid is 10.3 minutes, R$_t$ for 3-fluorobenzoic acid is 11.4 minutes). After approximately 4–6 hours the reaction is cooled to room temperature when the ratio of methyl ester to acid is greater than 95 to 5. The resulting title compound in solution can be used directly in the following designated reactions.

EXAMPLE 2

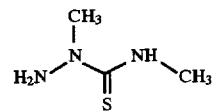

Preparation of 2,4-Dimethylthiosemicarbazide

A 1-L, three-necked, round-bottomed flask, equipped with a thermometer, addition funnel, reflux condenser, magnetic stirring bar and nitrogen bubbler is charged with methyl hydrazine (77.94 g, 90 mL, 1.69 mol) and isopropanol (440 mL). The solution is heated to approximately 40° C. with a heating mantle. The heating mantle is turned off and a solution of methyl isothiocyanate (126.6 g, 1.73 mol dissolved in 300 mL of isopropanol) is immediately added to the solution via the addition funnel over 1.75 hours. During the addition the temperature of the reaction increases to 55° C., the color of the reaction changes from yellow to green and a white precipitate begins to form after addition of approximately ⅓ of the methyl isothiocyanate solution. After addition of the methyl isothiocyanate solution is complete, the reaction is cooled to room temperature and then stored in a freezer at −5° C. for 16 hours. The white solid is collected using a medium sintered glass funnel, washed with isopropanol (2×50 mL) and dried overnight under vacuum at room temperature to provide the title compound (170.5 g, 85%); mp 135°–137° C.

EXAMPLE 3

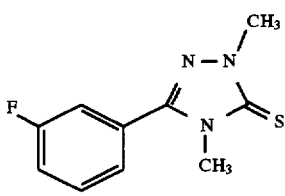

Preparation of 5-(3-Fluorophenyl)-2,4-dimethyl-3H-1,2,4-triazole-3-thione

Small scale example

Scheme I; A 250-mL, three-necked, round-bottomed flask, equipped with an addition funnel, reflux condenser, thermometer, magnetic stirring bar, and nitrogen bubbler is charged with 2,4-dimethylthiosemicarbazide (50.0 mmol, prepared in example 2), 20% aqueous sodium hydroxide (150 mmol) and toluene (100 mL). The caustic slurry of 2,4-dimethylthiosemicarbazide is then heated to 80° C. and 3-fluorobenzoyl chloride (51.0 mmol, obtained from Aldrich Chemical Company, Inc.) dissolved in toluene (50 mL) is added to the slurry via the addition funnel over a period of 30 minutes. After addition of the 3-fluorobenzoyl chloride is complete, the reaction is allowed to stir at 80° C. for one hour. Throughout the reaction and post-reaction period, the mixture is easily stirred and few solids from the insoluble intermediate are observed. The reaction mixture is then cooled to room temperature and transferred to a separatory funnel. The layers are separated and the organic layer is washed with water (2×50 mL). The organic layer is then concentrated under vacuum to provide the title compound (96% yield). The title compound is crystallized by dissolving the solid residue in hot isopropanol (65 mL) and filtering while hot through fluted filter paper into a flask which contains refluxing isopropanol (10 mL). The solution is then cooled to −5° C. for more than 2 hours. The resulting solid is collected by filtration through a medium sintered glass funnel, the solid is washed with isopropanol (10 mL) and dried overnight under vacuum at room temperature to provide the title compound (>90% yield).

Alternatively, the above reaction can be performed in an analogous manner, utilizing the 3-fluorobenzoyl chloride prepared in example 1, to provide the title compound (90% yield).

Scale-Up Example for the Preparation of the Title Compound

Scheme I; A 1-L reaction vessel is charged with 2,4-dimethylthiosemicarbazide (37.35 g, 313 mmol, prepared in example 2), toluene (539.5 g) and 20% aqueous sodium hydroxide (188.7 g). The caustic slurry of 2,4-dimethylthiosemicarbazide is then heated to 80° C. and 3-fluorobenzoyl chloride (51.1 g, 322 mmol) is added over 30 minutes. After addition of the 3-fluorobenzoyl chloride is complete, the reaction is stirred at 80° C. for 1 hour. It is then cooled to 50° C. and the aqueous layer (195.1 g) is decanted off. Water (150 mL) is added to the reaction vessel with mixing, the layers are then allowed to separate and the aqueous wash (154.4 g) is decanted off. Again, water (150 mL) is added with mixing to the reaction vessel, the layers are then allowed to separate and the aqueous wash (145.4 g) is decanted off leaving the washed organic layer (605.6 g). Most of the remaining toluene (427.3 g) is then distilled (78° C. at 290 mm Hg) from the organic layer. Isopropanol (625 mL) is added to the reaction vessel, the mixture is heated to 45° C. and then cooled at a rate of about 0.1° C./minute to 25° C. Nucleation occurs at about 41.3° C. It is then cooled at a rate of about 0.3° C./minute to −15° C. The title compound is then collected by vacuum filtration and is rinsed with isopropanol (50 mL). The solid is dried under vacuum (0.3 mm Hg) at room temperature for 16 hours to provide the title compound (57.67 g, 82.4%). Analysis of the mother liquor reveals 8.14 g of additional title compound and 92.6 g of toluene. Analysis of the isopropanol wash of the collected solid reveals 0.32 g of title compound and 0.52 g of toluene. Thus the total amount of title compound prepared is 66.13 g (94.5%).

Large Scale Preparation of the Title Compound

In an appropriate reactor, toluene (77.6 Kg) and 2,4-dimethylthiosemicarbazide (5.44 Kg, 45.7 mol) are combined. The contents of the reactor are agitated and heated to about 50° C. Aqueous sodium hydroxide (21.8 Kg of a 25% aqueous solution) and water (7.6 Kg) are added. The reaction mixture is then heated to 78° C. 3-fluorobenzoyl chloride (7.35 Kg, 46.4 mol) is then slowly added to the reaction mixture. After addition of the acid chloride is complete, the reaction is allowed to stir for 1 hour at 80° C. The reactor is then cooled to 50° C. and the resulting two phases are separated. The organic phase is washed with water (39.7 Kg) and the majority of the toluene is then removed by vacuum distillation. Isopropyl alcohol (65.3 Kg) is then added and the reaction mixture is heated to 78° C. and filtered. The solution is then cooled to −15° C. The resulting solid is collected by centrifugation and is dried to provide the title compound (8.67 Kg, 85%).

EXAMPLE 4

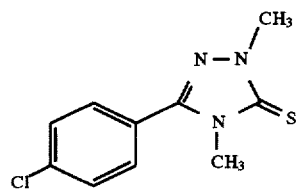

Preparation of 5-(4-Chlorophenyl)-2,4-Dimethyl-3H-1,2,4-Triazole-3-Thione

Scheme I; The title compound can be prepared in a manner analogous to either the small scale or the scale-up example described in example 3, utilizing 2,4-dimethylthiosemicarbazide and 4-chlorobenzoyl chloride as starting materials.

As with any group of structurally related compounds which possesses a particular generic utility, certain groups are preferred for compounds of formula (I) in the end-use application.

Compounds of formula (I) wherein n is the integer 1 are generally preferred. Compounds of formula (I) wherein R is in the meta position (3 position) on the phenyl ring are generally preferred. Compounds of formula (I) wherein R is a fluorine atom are generally preferred. Compounds of formula (I) wherein $R_2$ and $R_3$ are methyl are generally preferred.

What is claimed is:

1. A process for preparing a compound of the formula:

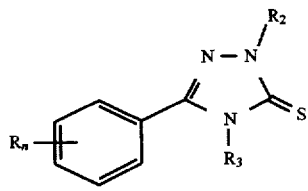

wherein

R is halogen, $C_{1-3}$ alkyl or $C_{1-3}$ alkoxy;

n is the integer 1 or 2; and $R_2$ and $R_3$ are each independently $C_{1-3}$ alkyl, comprising:

a) mixing a compound of the formula:

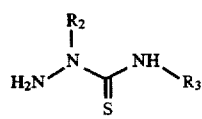

wherein $R_2$ and $R_3$ are defined as above, with a base and an organic solvent;

b) agitating the mixture at a temperature of about 22° C. to reflux; and c) adding about one molar equivalent of a compound of the formula:

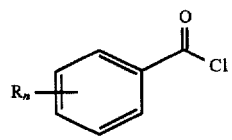

wherein R and n are defined as above, to the mixture.

2. A process according to claim 1 wherein the mixture is heated at a temperature of about 80° C.

3. A process according to claim 1 wherein the organic solvent is toluene.

4. A process according to claim 1 wherein the base is aqueous sodium hydroxide.

5. A process according to claim 4 wherein the concentration of aqueous sodium hydroxide is about 20%.

6. A process according to claim 1 wherein the number of equivalents of base is 3.

7. A process according to claim 1 wherein the number of equivalents of base is 2.

8. A process according to claim 2 wherein the organic solvent is toluene and the base is aqueous sodium hydroxide.

9. A process according to claim 1 wherein the compound prepared is 5-(3-fluorophenyl)-2,4-dimethyl-3H-1,2,4-triazole-3-thione.

10. A process according to claim 9 wherein the base is 20% aqueous sodium hydroxide.

11. A process according to claim 9 wherein the organic solvent is toluene, the base is 20% aqueous sodium hydroxide, the number of equivalents of the base is 3 and the mixture is heated at a temperature of about 80° C.

12. A process according to claim 9 wherein the organic solvent is toluene, the base is 25%, aqueous sodium hydroxide, the number of equivalents of the base is about 2.2 and the mixture is heated at a temperature of about 80° C.

* * * * *